United States Patent [19]

Veber et al.

[11] 4,192,875
[45] Mar. 11, 1980

[54] CYCLIC HEXAPEPTIDE

[75] Inventors: Daniel F. Veber, Ambler; Roger M. Freidinger, Hatfield, both of Pa.

[73] Assignee: Merck & Co., Inc., Rahway, N.J.

[21] Appl. No.: 8,904

[22] Filed: Feb. 2, 1979

[51] Int. Cl.$^2$ ............... A61K 31/365; A61K 41/435; C07D 210/00
[52] U.S. Cl. ................................ 424/256; 424/267; 260/239.3 P; 546/243
[58] Field of Search ............................ 424/256, 267; 260/239.3 P; 546/243

[56] References Cited
U.S. PATENT DOCUMENTS 4,108,987 8/1978 Veber et al. ................. 260/112.5 R

*Primary Examiner*—Delbert R. Phillips
*Attorney, Agent, or Firm*—David L. Rose; Harry E. Westlake

[57] ABSTRACT

Synthetic novel cyclic hexapeptide having the structure:

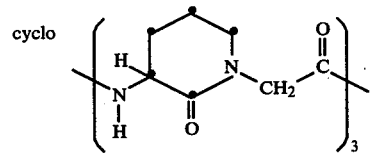

and the dipeptide

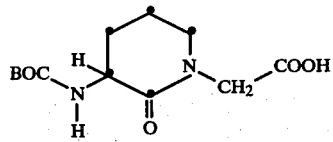

are prepared. Oral administration of these peptides improves the digestive efficiency of certain herbivorous animals.

7 Claims, No Drawings

CYCLIC HEXAPEPTIDE

BACKGROUND OF THE INVENTION

For many years, the animal science industry has tried to increase the efficiency of feed utilization in both ruminant and non-ruminant animals. More study has been done in ruminant animals because of their greater economic importance.

In the course of investigating the efficiency of feed use, the mechanism by which ruminants digest and degrade the components of their feed to form molecules which can be metabolically utilized has been intensively studied. Aspects of the mechanism of carbohydrate utilization are now known. Microorganisms in the rumen of the animal ferment carbohydrates to produce monosaccharides, and then degrade the monosaccharides to pyruvate.

Pyruvate is then metabolized by microbiological processes to either acetate or propionate, which may be either acids or derivatives of the acids. Two acetates may be combined thereafter, still in the rumen, to form butyrate. Leng, "Formation and Production of Volatile Fatty Acids in the Rumen." Physiology of Digestion and Metabolism in the Ruminant (Phillipson et al., ed.), Oriel Press, pp. 408–410.

The animal can utilize butyrate, propionate, and acetate with differing degrees of efficiency. (Smith, Gary E., 1971. Energy Metabolism and Metabolism of Volatile Fatty Acids, Digestive Physiology and Nutrition of Ruminants. O.S.U. Book Stores. Corvallis, Oreg.). Utilization of these compounds, which are collectively known as volatile fatty acids (VFA), occurs after absorption from the gut of the animal. Butyrate is utilized most efficiently, and acetate the least efficiently. However, the relative efficiency of use of butyrate is negated by the inefficiency of the manufacture of butyrate, which must be made from acetate in the rumen.

The process of formation of acetate in the rumen is one of the major inefficiencies in the rumen. Since acetate is made by the degradation of a pyruvate molecule, each molecule of acetate which is produced is accompanied by a one carbon molecule which subsequently results in the formation of methane. Most of the methane produced is lost through eructation. Since butyrate is made from two molecules of acetate, each molecule of the relatively efficiently used butyrate involves the loss to the animal of two molecules of methane, with all of the associated energy.

Thus, the efficiency of carbohydrate utilization (carbohydrates being the major nutritive portion of ruminant animals' feed) can be increased by treatments which encourage the animal to produce propionate and butyrate rather than acetate from carbohydrates. Further, the efficiency of feed use can be effectively monitored by observing the production and concentration of propionate compounds in the rumen. If the animal is making more propionates, it will be found to be using its feed more efficiently.

The efficiency of feed utilization by a ruminant animal can readily be determined by chemical analysis for acetate and propionate produced by the fermentation occurring in the rumen or more conveniently by chemical analysis of the rumen contents for acetate and propionate using an in vitro rumen fermentation test.

DESCRIPTION OF THE INVENTION

It is the object of the present invention to provide a novel cyclic hexapeptide having the structure:

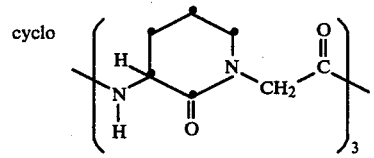

and the dipeptide

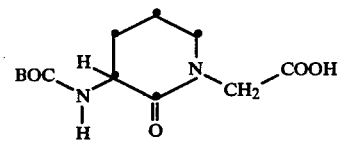

The preferred compounds of the present invention are:

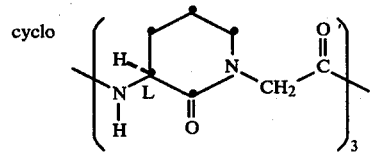

and the dipeptide

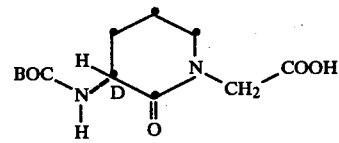

which are useful for improving ruminant feed utilization.

It is a further object of the present invention to provide for feed compositions useful in improving feed utilization. A further aspect of the present invention is a method of improving feed utilization by ruminants having a developed rumen function which comprises oral administration to the ruminants of an effective VFA-increasing amount of the above mentioned novel peptides. A still further aspect of the present invention is the process for the synthetic preparation of the novel peptides of the present invention.

The peptides of the present invention are useful to ruminants which have a developed rumen function. Young ruminants, basically those still unweaned, function as monogastric animals. They use their simple liquid feeds just as monogastric animals do. As the young ruminants begin to eat solid feed containing cellulose, starch, and other carbohydrates, the function of the rumen begins to develop, and the microbiological population of the rumen increases. After the animal has eaten solid feed for a time, its rumen reaches its full development and continues to operate throughout the animal's life.

The present invention is functional in all of the ruminants, that is, the animals which have multiple stomachs, one of which is a rumen. The economically important ruminant animals are cattle, sheep and goats.

Herein below, in the further description of the synthesis of the peptides, the reagents used will be first listed by their chemical name and their common abbreviation in parenthesis. Thereafter, the reagent will be referred to by the common abbreviation.

For convenience, a table of relevant abbreviations is provided:

| Abbreviated Designation | Protecting Groups |
|---|---|
| BOC | tert-butyloxycarbonyl |
| CBZ | benzyloxycarbonyl |

| Abbreviated Designation | Condension Agents |
|---|---|
| DPPA | diphenylphosphorylazide |

| Abbreviated Designation | Solvents |
|---|---|
| DMF | dimethylformamide |
| MeOH | methanol |
| EtOAc | ethyl acetate |
| HOAc | acetic acid |
| DMSO | dimethylsulfoxide |

In accordance with the present invention, the novel cyclic hexapeptide is prepared by cyclotrimerization of the monomeric dipeptide amino acid having the structure:

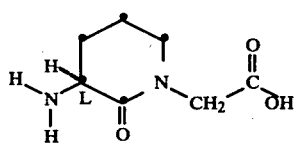

The monomer is synthesized in three steps from a commercially available protected ornithine derivative by the following process and cyclized:

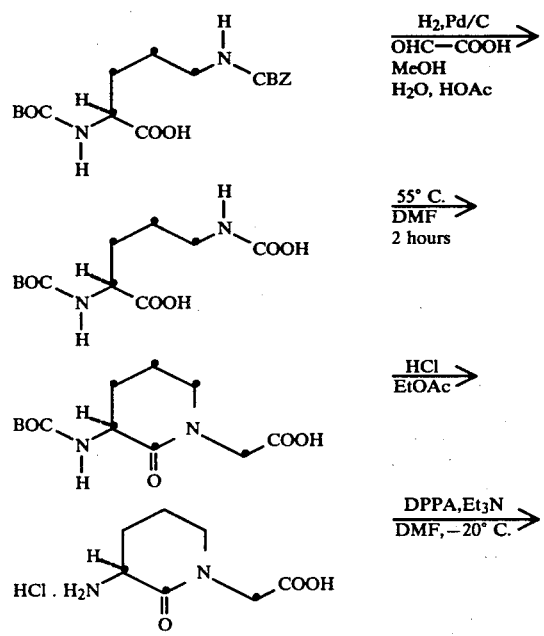

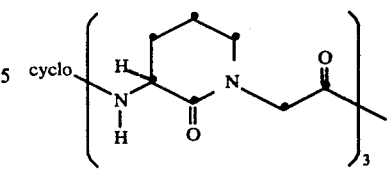

The following Examples illustrate methods of carrying out the present invention, but it is to be understood that these Examples are given for purposes of illustration and not of limitation.

EXAMPLE 1

Preparation of $N^\alpha$-tert-butyloxycarbonyl-$N^\delta$-carboxymethyl-L-ornithine The following quantities of reagents were mixed and hydrogenated on a Parr apparatus for 16 hours:

| | | |
|---|---|---|
| $N^\alpha$-tert-butyloxycarbonyl-$N^\delta$-benzyloxycarbonyl-L-ornithine as prepared by the process set forth in T. Kato, et al., Bull. Chem. Soc. Jap., 39, 2242 (1966) | 11 g | (0.03 mole) |
| glyoxylic acid hydrate | 6.7 g | |
| 10% palladium on carbon catalyst | 1.0 g | |
| methanol | 50.0 ml | |
| water | 35.0 ml and | |
| acetic acid | 5.0 ml | |

The mixture was filtered through Supercel, and the filtered catalyst was washed with 1:1 methanol-water. The filtrate and washings were concentrated in vacuo to a white foam which was crystallized from methanol-ether to give 4.66 g (54%) of fine needles, mp 150° C. (dec.): ir (nujol) 3300, 1730, 1690 cm$^{-1}$; nmr (d$_6$-DMSO) $\delta 1.37$ (s,9), 1.65 (m,4), 2.82 (m,2), 3.32 (m,2), 3.83 (m,1), 7.78 (br.d,1), 9.30 (br.s,3); [$\alpha$]$_{589}^{24}$ 2.59° (c, 0.966, MeOH).

Anal. calc'd. for $C_{12}H_{22}N_2O_6$; Calc'd.: C, 49.65; H, 7.64; N, 9.65; Found: C, 49.54; H, 7.60; N, 9.99.

EXAMPLE 2

Preparation of L-1-Carboxymethyl-3-tert butyloxycarbonylamino-2-piperidone

A sample of $N^\alpha$-tert-butyloxycarbonyl-$N^\delta$-carboxymethyl-L-ornithine (21.6 g, 74.5 mmole), prepared by the process set forth in Example 1, was suspended in dimethylformamide (700 ml) and stirred with heating at 55° C. under nitrogen for 2 hours. Complete solution occurred within 40 minutes. The solution was cooled and concentrated in vacuo to an oil which crystallized from ethyl acetate-hexane to give 19.06 g (94%) of white crystals, mp 111°-113° C.; ir (smear) 3300, 2950, 1720, 1660 cm$^{-1}$; nmr (CDCl$_3$) $\delta 1.43$ (s,9), 1.67-2.57 (m,4), 3.83 (m,2), 4.07 (m,3), 5.63 (m,1), 10.37 (m,1); [$\alpha$]$_{589}^{24}$ −22.14° (c, 0.998, MeOH).

Anal. calc'd. for $C_{12}H_{20}N_2O_5$; Calc'd.: C, 52.93; H, 7.40; N, 10.29; Found: C, 52.99; H, 7.47; N, 10.28.

EXAMPLE 3

Preparation of
L-1-Carboxymethyl-3-amino-2-piperidone
hydrochloride

A sample of L-1-carboxymethyl-3-tert-butyloxycarbonylamino-2-piperidone (7.5 g, 27.6 mmole), prepared by the process set forth in Example 2, was suspended in 350 ml of ethyl acetate under nitrogen. The mixture was cooled to 0° C. and anhydrous hydrogen chloride was bubbled through for 20 minutes followed by nitrogen for 1.5 hours. The mixture was filtered, and the solid was washed with a small portion of ethyl acetate and dried in vacuo to a white powder (4.83 g, 84%): nmr ($d_6$-DMSO) $\delta$1.88 (m), 3.33(m), 3.82(m), 4.02(s), 8.60(m); mass spectrum (70 eV)/m/e 172(M+—HCl); $[\alpha]_{589}^{24} -1.84°$ (c,0.980, MeOH).

EXAMPLE 4

Preparation of
cyclo-[(L-1-Carboxymethyl-3-amino-2-piperidone)yl]$_3$

A sample of L-1-carboxymethyl-3-amino-2-piperidone hydrochloride (5.34 g, 25.6 mmole), prepared by the process set forth in Example 3, was dissolved in 250 ml of freshly degassed dimethylformamide and the pH as measured by narrow range indicator paper was adjusted to 7.4 with triethylamine (4.5 ml). The mixture was cooled to $-25°$ C. and diphenylphosphorylazide (5.5 ml, 25.6 mmole) was added with vigorous stirring. The reaction was stored at $-20°$ C. for 3 days, at 5° C. for 1 day, and at room temperature for 1 day with periodic pH adjustments with triethylamine (6 ml). The mixture was filtered and concentrated in vacuo. The residue was dissolved in 3:1 dimethylformamide-water and stirred with 150 ml of Bio-Rad AG501-X8(D) mixed bed ion exchange resin for 2 hours. The mixture was filtered and the filtrate concentrated in vacuo. The residue crystallized and the crystals were rinsed with 1:1.5 methylene chloride-ethyl acetate and filtered to give 1.02 g (26%): nmr (CDCl$_3$) $\delta$1.0–2.1 (m,9), 2.3–2.7 (m,3), 3.09 (d,3, J=15 Hz), 3.33 (m,6), 4.16 (quintet, 3, J=5 Hz), 4.85 (d,3, J=15 Hz), 7.64 (d,3, J=5 Hz); mass spectrum (70 eV) m/e 462 (M+); gel filtration on Sephadex G-25 (50% HOAc) supports monomeric structure.

EXAMPLE 5

Preparation of
D-1-Carboxymethyl-3-tert-butyloxycarbonylamino-2-piperidone

Substitution of an equivalent amount of $N^\alpha$-tert-butyloxycarbonyl-$N^\delta$-benzyloxycarbonyl-L-ornithine with the D-isomer, $N^\alpha$-tert-butyloxycarbonyl-$N^\delta$-benzyloxycarbonyl-D-ornithine in Example 1 provides $N^\alpha$-tert-butyloxycarbonyl-$N^\delta$-carboxymethyl-D-ornithine.

Treatment of $N^\alpha$-tert-butyloxycarbonyl-$N^\delta$-carboxymethyl-D-ornithine by the process of Example 2 provides the desired D-1-carboxymethyl-3-tert-butyloxycarbonylamino-2-piperidone.

EXAMPLE 6

Applying the process of Example 3 and 4 to D-1-carboxymethyl-3-tert-butyloxycarbonylamino-2-piperidone yields cyclo-[(D-1-carboxymethyl-3-amino-2-piperidone)yl]$_3$.

The effectiveness of the peptides of the present invention in modifying the ratio of volatile fatty acids produced in the rumen is illustrated by means of in vitro tests as set forth below.

In Vitro Rumen Fermentation Test

Rumen fluid which contained methane-producing bacteria and other rumen bacteria was produced in a fermentor which was set up and maintained to simulate the conditions of a rumen.

The test was carried out in a screw-cap tube which was sealed with a butyl rubber stopper. The tube contained an incubation mixture consisting of 100 mg ground feed, 0.5 ml buffer-salts solution, 3.5 ml rumen fluid which had been strained through 4 layers of absorbent gauze and 1 mg of the test compound. The air in the tube was replaced with a gas mixture of 97% nitrogen-3% hydrogen made free of oxygen by passage through a catalytic purifier. After incubation for 18 hours in a water bath shaker at 39° C., 0.5 ml of the gas was removed through the stopper into the sample loop of a Fisher Gas Partitioner. The gas sample was partitioned, and the methane produced was compared to a standard gas mixture containing a known amount of methane. The incubation mixture was acidified with 4 ml of 10% metaphosphoric acid and centrifuged. One $\mu$l of the supernatant was analyzed by gas-liquid chromatography. The volatile fatty acids were compared to a standard volatile fatty acid mixture containing known amounts of acetic, propionic, butyric and valeric acids. Appropriate controls were included.

| Compound | Dose | % Inhibition of Methane Prodution |
|---|---|---|
| BOC-NH-[piperidone-D]-N-CH$_2$-COOH | 250 $\mu$g/ml | 69% |

-continued

| Compound | Dose | % Inhibition of Methane Prodution |
|---|---|---|
| cyclo-[NH-CH(L)-C(=O)-N(CH₂-C(=O))-]₃ (with H on N) | 20 µg/ml | 50% |

Both compounds were effective in increasing the production of the VFAs, propionic, butyric and valeric at the expense of methane and acetate.

Administration of the peptides of the present invention prevents and treats ketosis as well as improves feed utilization.

It has been found that the peptides of the present invention used in this novel method increase the efficiency of feed utilization in ruminant animals. The easiest way to administer the compounds is by mixing them in the animal's feed.

However, the compounds can be usefully administered in other ways. For example, they can be incorporated into tablets, drenches, salt blocks for pasture use, paste, boluses, or capsules and dosed to the animals. Formulation of the compounds in such dosage forms can be accomplished by means of methods well known in the veterinary pharmaceutical art. Each individual dosage unit should contain a quantity of the feed-efficiency-improving compound which has a direct relation to the proper daily dose for the animal to be treated.

Capsules are readily produced by filling gelatin capsules with any desired form of the desired compound. If desired, the compound can be diluted with an inert powdered diluent. Tablets of the compounds useful in this novel method are made by conventional pharmaceutical processes. Manufacture of tablets is a well-known and highly-advanced art. In addition to the active ingredient, a tablet usually contains a base, a disintegrator, an absorbent, a binder, and a lubricant.

Drenches of the compounds are prepared most easily by choosing a water-soluble form of the compound. If an insoluble form is desired for some reason, a suspension may be made. Alternatively, a drench may be formulated as a solution in a physiologically-acceptable solvent such as a polyethylene glycol.

Suspensions of insoluble forms of the compound can be prepared in non-solvents such as vegetable oils such as peanut, corn or sesame oil; in a glycol such as propylene glycol or a polyethylene glycol; or in water, depending on the form of the compound chosen.

These compounds may also be administered in the drinking water of the ruminants. Incorporation into drinking water is performed by adding a water soluble or water-suspendable form of desired compounds in the water in the proper amount. Formulation of the compounds for addition to drinking water follows the same principles as formulation of drenches.

In the field the active ingredients may be administered by means of salt or molasses blocks. A typical block may be prepared using the following ingredients:

| Ingredient | Weight percent |
|---|---|
| Dried cane molasses | 44.54 |
| Ground soybean hulls | 24.90 |
| Cyclo-[NH-CH(L)-C(=O)-N(CH₂-C(=O))-]₃ | 10.00 |
| Granulated salt | 21.59 |
| Trace minerals and vitamins | 0.20 |
| Stabilized animal fat | 1.11 |
| Moisture | 2.66 |

The most practical way to treat animals with the compounds of this invention is by the formulation of the compounds into the feed supply. Any type of feed may be medicated with the compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about 0.1 to 50% by weight of the active compound. Especially preferred are premixes containing 2 to 25% by weight of the active compound. The wide range results from the wide range of concentration of compound which may be desired in the final feed. Premixes may be either liquid or solid.

The formulation of ruminant feeds containing the proper amounts of the compounds for useful treatment is mainly a matter of arithmetic. It is necessary only to calculate the amount of compound which is desired to administer to each animal, to take into account the amount of feed per day which the animal eats, and the concentration of compound in the premix to be used, and calculate the proper amount of premix to be blended into the final feed.

The peptides of this invention find their primary use in the treatment of ruminants such as sheep and cattle. The optimum amount of the cyclic peptide to be employed for the treatment of a particular animal, will depend on the particular peptide employed, the species of animal to be treated, and the weight of the animal. Generally, good results are obtained with the peptides of this invention by the oral administration of feed containing from about 0.00005 to about 0.5% of the peptides, the preferred range being about 0.00025 to about 0.1%. Excellent improvement of feed utilization is obtained in cattle and sheep by administering feed containing from about 0.0025 to about 0.01% of the active ingredient.

All of the methods of formulation, mixing, and pelleting feeds which are normally used in the ruminant feed art are entirely appropriate for manufacturing feed containing the compounds usable in this method.

It is not intended that the scope of this invention be limited to any particular formulations or methods of administration. The invention is a method of increasing the efficiency of feed utilization by ruminant animals by the oral administration of certain compounds, regardless of the method of administration of the compounds.

What is claimed is:

1. The cyclic hexapeptide having the structure:

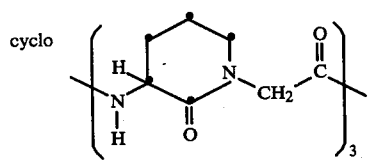

and the dipeptide

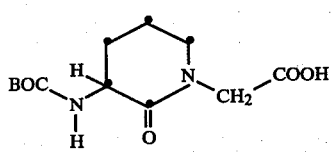

2. The cyclic hexapeptide according to claim 1 having the structure:

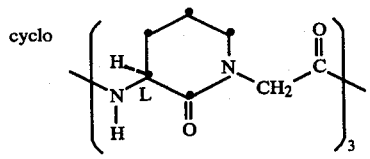

and the dipeptide

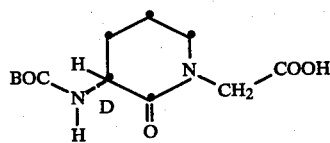

3. A composition useful for increasing the efficiency of feed utilization by ruminant animals having a developed rumen function comprising an inert carrier and a VFA-increasing amount of the peptide having the structure:

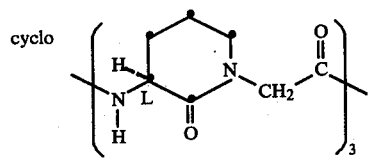

and the dipeptide

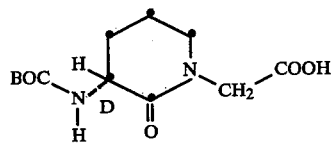

4. A composition according to claim 3 wherein said compound comprises from about 0.00005 to about 0.5% by weight of said composition.

5. A composition according to claim 3 wherein said compound comprises from about 0.00025 to about 0.1% by weight of said composition.

6. A concentrated premix composition for addition to the feed of a ruminant, useful for the increased utilization of feed, which comprises from about 0.1 to about 50% by weight of the peptide having the structure:

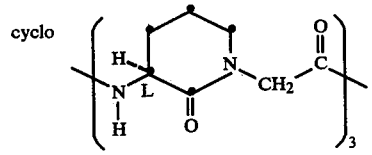

and the dipeptide

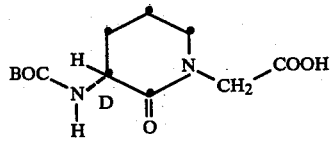

7. The concentrated premix composition of claim 6 which comprises from about 2 to about 25% by weight of said peptide.

* * * * *